(12) United States Patent
Goto et al.

(10) Patent No.: US 10,996,211 B2
(45) Date of Patent: May 4, 2021

(54) MEASURING REAGENT AND ANALYSIS DEVICE FOR ANALYZING BIOPOLYMER

(71) Applicant: HITACHI HIGH-TECHNOLOGIES CORPORATION, Tokyo (JP)

(72) Inventors: Yusuke Goto, Tokyo (JP); Takahide Yokoi, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 137 days.

(21) Appl. No.: 15/777,326

(22) PCT Filed: Oct. 20, 2016

(86) PCT No.: PCT/JP2016/081061
§ 371 (c)(1),
(2) Date: May 18, 2018

(87) PCT Pub. No.: WO2017/110226
PCT Pub. Date: Jun. 29, 2017

(65) Prior Publication Data
US 2018/0335417 A1    Nov. 22, 2018

(30) Foreign Application Priority Data
Dec. 24, 2015   (JP) .............................. JP2015-251426

(51) Int. Cl.
*G01N 33/487*     (2006.01)
*G01N 27/447*     (2006.01)
(Continued)

(52) U.S. Cl.
CPC ..... *G01N 33/48721* (2013.01); *G01N 33/483* (2013.01); *G01N 15/1031* (2013.01); *G01N 27/44791* (2013.01)

(58) Field of Classification Search
CPC ................... G01N 33/48721; G01N 27/44791
See application file for complete search history.

(56) References Cited

U.S. PATENT DOCUMENTS

| 5,795,782 | A |   | 8/1998 | Church et al. |
| 6,048,553 | A | * | 4/2000 | Beckett ............... A61P 29/00 424/686 |

(Continued)

FOREIGN PATENT DOCUMENTS

| JP | 2006-113057 A | 4/2006 |
| JP | 2015-514128 A | 5/2015 |

(Continued)

OTHER PUBLICATIONS

M.J. Fedor and J.R. Williamson, The Catalytic Diversity of RNAs, 6 Nature Reviews Molecular Cell Biology, 2005, p. 399-412. (Year: 2005).*

(Continued)

*Primary Examiner* — Luan V Van
*Assistant Examiner* — Caitlyn Mingyun Sun
(74) *Attorney, Agent, or Firm* — Mattingly & Malur, PC (57) ABSTRACT

An object of the present invention is to solve inhibition of biopolymer measurement in a nanopore, which involves three-dimensional conformation of a biopolymer containing a nucleic acid. The present invention provides a device for analyzing a biopolymer containing a nucleic acid, the device including: an array device including a plurality of thin film parts having a nanopore; a single common container and a plurality of individual containers capable of storing a measurement solution which is brought into contact with the thin films; and individual electrodes respectively provided in the plurality of individual containers, wherein: the measurement solution is introduced into each of the individual containers and the common container so as to be brought into contact with the thin films; and the measurement solution has a pH equal to or greater than pKa of a guanine base and contains cesium ions as electrolyte cations.

9 Claims, 7 Drawing Sheets

(51) Int. Cl.
   *G01N 33/483* (2006.01)
   *G01N 15/10* (2006.01)

(56) References Cited

U.S. PATENT DOCUMENTS

| | | | |
|---|---|---|---|
| 8,105,846 B2* | 1/2012 | Bayley | G01N 33/48721 436/518 |
| 2005/0095599 A1 | 5/2005 | Pittaro et al. | |
| 2006/0073489 A1 | 4/2006 | Li et al. | |
| 2011/0000788 A1* | 1/2011 | Deschamps | G01N 27/44747 204/451 |
| 2015/0140104 A1* | 5/2015 | Ashford | C07D 403/12 424/489 |
| 2016/0244823 A1 | 8/2016 | Yoshida et al. | |

FOREIGN PATENT DOCUMENTS

| | | |
|---|---|---|
| WO | 2013/153359 A1 | 10/2013 |
| WO | 2015/068673 A1 | 5/2015 |

OTHER PUBLICATIONS

Kimberly Venta et al., "Differentiation of Short, Single-Stranded DNA Homopolymers in Solid-State Nanopores," ACS NANO, Apr. 26, 2013, vol. 7, No. 5, pp. 4629-4636.
Min-Hyun Lee et al., "A Low-Noise Solid-State Nanopore Platform Based on a Highly Insulating Substrate," Scientific Reports, 4:7448; DOI 10.1038/srep07448, Dec. 12, 2014.
International Search Report for PCT/JP2016/081061 dated Jan. 10, 2017.
Great Britain Office Action received in corresponding Great Britain Application No. GB1808081.2 dated Jun. 1, 2020.
Vinograd, J. et al., "The Buoyant Behaviour of Viral and Bacterial DNA in Alkaline CsC", PNAS, Dec. 3, 1962, pp. 12-17, vol. 49, Gates and Crellin Laboratories of Chemistry and Norman W. Church Laboratory of Chemical Biology, California Institute of Technology.

\* cited by examiner

GUANINE QUADRUPLEX

(b)

DEPROTONATED (c)

GUANINE QUADRUPLEX           SINGLE-STRANDED pH = 9.2
(Guanine pKa (N-1 position))

MEASURING REAGENT AND ANALYSIS DEVICE FOR ANALYZING BIOPOLYMER

TECHNICAL FIELD

The present invention relates to a measurement reagent, a device and a method for analyzing an object to be measured, in particular, a biopolymer containing a nucleic acid (DNA and the like), using a pore embedded in a thin film.

BACKGROUND ART

When a solution containing an electrolyte is brought into contact with a pore having a diameter of about 0.9 nm to several nanometers (hereinafter referred to as a nanopore) and embedded in a thin film having a thickness of about several angstroms to several tens of nanometers, and a potential difference is applied across the thin film, the solution containing the electrolyte can be passed through the nanopore. At this time, when an object to be measured passes through the nanopore, the electrical characteristics, in particular, the resistance value, of the periphery part of the nanopore change, whereby the object to be measured can be detected and analyzed by detecting a change in the electrical characteristics. When the object to be measured is a biopolymer, the electrical characteristics of the periphery part of the nanopore change in a pattern form according to the monomer sequence pattern of the biopolymer. A method for analyzing the monomer sequence of the biopolymer utilizing the change has been actively studied in recent years. Among them, a system based on the principle that the amount of a change in ion current observed when a biopolymer passes through a nanopore varies depending on the kinds of monomers (blocked current method) is considered to be viable. In this case, since the analysis accuracy of the monomer sequence is determined by the amount of a change in ion current, a difference in ion current amount between monomers is desirably larger. Unlike a conventional method, the blocked current method can directly read a biopolymer without requiring a chemical procedure which involves fragmentation of the biopolymer. When the biopolymer is DNA, the blocked current method is a next-generation DNA nucleotide sequence analysis system. When the biopolymer is a protein, the blocked current method is an amino acid sequence analysis system. These are expected as systems capable of reading much longer sequence lengths than those of the conventional method.

There are two types of nanopore devices: a biopore device using a protein embedded in a lipid bilayer membrane and having a center pore; and a solid pore device having a pore formed in an insulating thin film formed by a semiconductor processing process. The biopore device uses a pore (diameter: 1.2 nm, thickness: 0.6 nm) of a modified protein (such as *Mycobacterium smegmatis* porin A (MspA)) embedded in a lipid bilayer membrane as a biopolymer detection part, to measure the amount of a change in ion current. On the other hand, in the solid pore device, there has been used a structure including a nanopore formed in a thin film made of silicon nitride which is a semiconductor material or a thin film consisting of a single molecule layer made of graphene or molybdenum disulfide.

In such analysis devices, as a basic unit, there has been used a device which includes a nanopore device, a solution containing an object to be measured and an electrolyte, and a pair of electrodes between which the nanopore device is sandwiched. Such a constitution is described in Patent Literature 1 and Non-Patent Literature 1, for example. A material which can perform an electron transfer reaction with the electrolyte in the solution (can perform an electrochemical oxidation-reduction reaction) is typically employed for the electrode. Specifically, a silver/silver chloride electrode is often used because of its electrochemical potential stability and high reliability. As the electrolyte, an aqueous potassium chloride solution under pH neutralization is most typically used. The reason is that chloride ions can perform an electron transfer reaction with the silver/silver chloride electrode, and potassium ions have electric mobility equal to that of chloride ions, whereby electric conductivity can be sufficiently secured. In the solid pore (semiconductor nanopore), reports have been made that the amount of blocked current of a homopolymer consisting of an adenine base, a cytosine base, or a thymine base is measured by using an aqueous potassium chloride solution under pH neutralization (Non-Patent Literature 1 and Non-Patent Literature 2).

PRIOR-ART LITERATURE

Patent Literature

Patent Literature 1: U.S. Pat. No. 5,795,782 B

Non-Patent Literature

Non-Patent Literature 1: Venta, K., et al., Differentiation of Short Single-Stranded DNA Homopolymers in Solid-State Nanopores, ACS Nano 7 (5), p. 4629-4636 (2013).

Non-Patent Literature 2: Lee, M., et al., A Low-Noise Solid-State Nanopore Platform Based on a Highly Insulating Substrate, Scientific Reports 4, 7448 (2014).

SUMMARY OF INVENTION

Technical Problem

When the conventional aqueous potassium chloride solution under pH neutralization is used, a biopolymer containing a nucleic acid forms a three-dimensional conformation, to block the nanopore, which disadvantageously inhibits the measurement of the biopolymer in the nanopore. Particularly in the presence of potassium ions, a guanine (G) base strongly forms a tetramer (G-quadruplex), to block the nanopore, which obstructs the measurement of the biopolymer. This makes it impossible to accurately measure the amount of blocked current derived from the guanine base. Such a problem is also mentioned in Non-Patent Literature 1, for example. In the conventional aqueous potassium chloride solution under pH neutralization, the difference in ion current amount between monomers in the nanopore is small, so that the degree of base separation is poor, which causes a problem that the analysis accuracy of the final monomer sequence decreases. For example, Non-Patent Literature 2 discloses results that the blocked current amounts of an adenine base, cytosine base, and thymine base in a homopolymer are overlapped.

Means to Solve Problem

As a result of intensive investigation by the present inventors to solve the above problems, the inventors unexpectedly found that the use of a measurement solution having a pH greater than pKa of a guanine base and containing cesium ions as electrolyte cations makes it possible to prevent the formation of a G-quadruplex, and accurately measure a biopolymer containing a nucleic acid. The inventors have obtained also the following findings: when the measurement solution is used, a difference in the amount of blocked current which can be distinguished depending on the types of the bases is shown. That is, the degree of base separation is good, and the sequence of a biopolymer containing a nucleic acid can be analyzed with high accuracy. Based on these findings, the present invention has been completed.

The present invention typically relates to a measurement reagent for analyzing a biopolymer containing a nucleic acid by passing the biopolymer through a nanopore formed in a thin film and analyzing the biopolymer based on a change in an electrical signal, the measurement solution containing a measurement solution which has a pH equal to or greater than pKa of a guanine base and contains cesium ions as electrolyte cations.

The present invention also relates to a device for analyzing a biopolymer containing a nucleic acid, the device including: a thin film having a nanopore; a pair of containers capable of storing a measurement solution so as to be brought into contact with the thin film; and a pair of electrodes provided in each of the containers, wherein: the measurement solution is introduced into each of the containers so as to be brought into contact with the thin film; and the measurement solution has a pH equal to or greater than pKa of a guanine base and contains cesium ions as electrolyte cations.

The present invention also provides a device for analyzing a biopolymer containing a nucleic acid, the device including: an array device including a plurality of thin film parts having a nanopore; a single common container and a plurality of individual containers capable of storing a measurement solution which is brought into contact with the thin films; and individual electrodes respectively provided in the plurality of individual containers, wherein: the measurement solution is introduced into each of the individual containers and the common container so as to be brought into contact with the thin films; and the measurement solution has a pH equal to or greater than pKa of a guanine base and contains cesium ions as electrolyte cations.

Furthermore, the present invention relates to a method for analyzing a biopolymer containing a nucleic acid using the aforementioned measurement solution or the analysis device.

The present invention also relates to a solution having a pH equal to or greater than pKa of a guanine base and containing cesium ions as electrolyte cations. Such a solution can be used in a method and a device for analyzing a biopolymer, for example, using a blocked current type nanopore.

Advantageous Effects of Invention

The present invention allows biopolymer measurement in the nanopore to be smoothly performed by eliminating the three-dimensional conformation of the biopolymer containing a nucleic acid. In particular, a tetramer of the guanine base (G-quadruplex) may be eliminated, which makes it possible to correctly measure the amount of blocked current derived from the guanine base. According to the present invention, an ionic current difference between monomers is increased and the degree of base separation can be improved, thereby improving the analysis accuracy of final monomer sequence. Therefore, the measurement reagent, the analysis device, and the analysis method according to the present invention are useful in the fields of analysis of the biopolymer containing a nucleic acid, and test, diagnosis, therapy, drug discovery, and fundamental research and the like utilizing the analysis.

The problems, constitutions, and effects other than those described above are apparent from the descriptions of the following embodiments.

DESCRIPTION OF EMBODIMENTS

Figure 2:
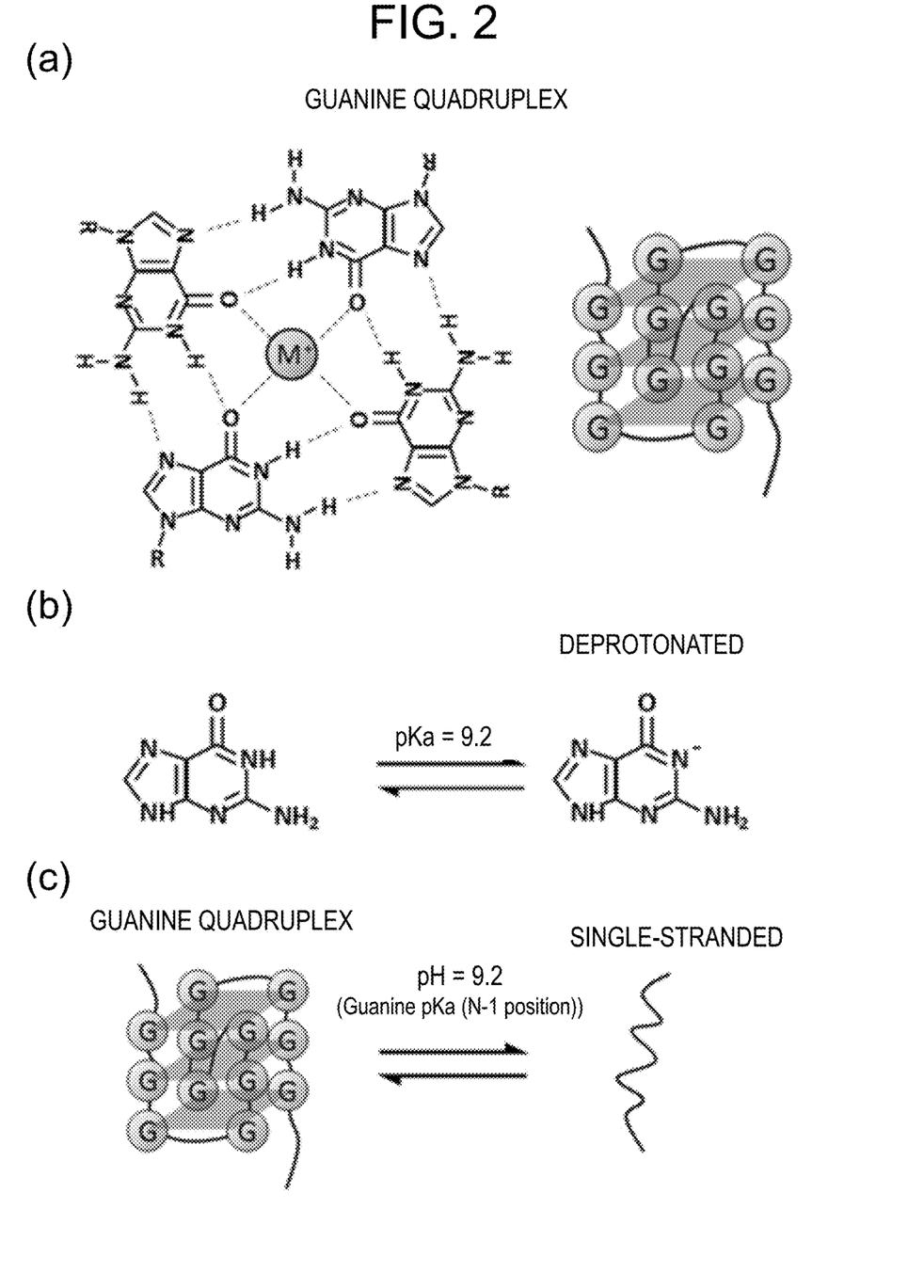
FIG. 2 is a diagram showing a mechanism of eliminating a guanine tetramer (G-quadruplex) according to the present invention.
Figure 3:
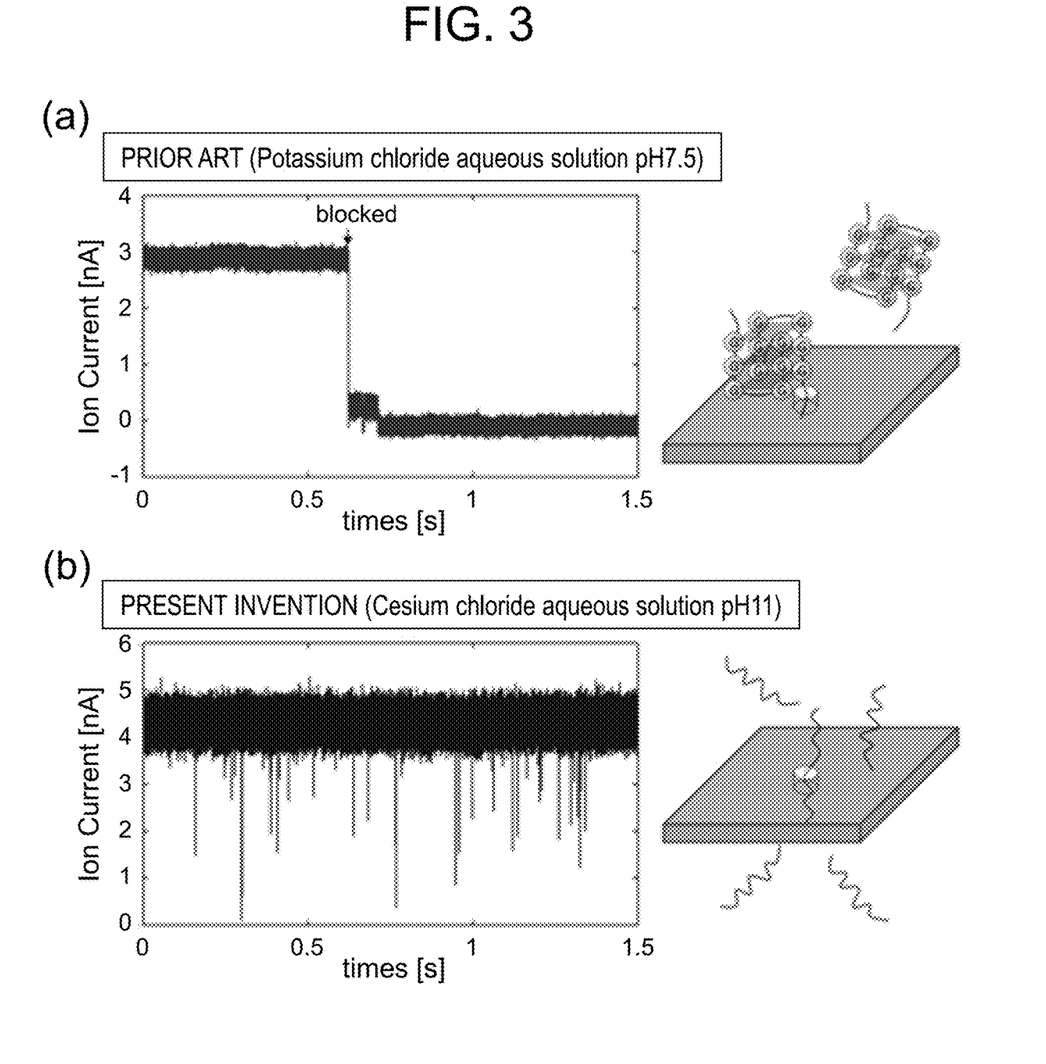
FIG. 3 is a diagram showing experimental results supporting an effect of the present invention when compared with that of the prior art.
Figure 4:
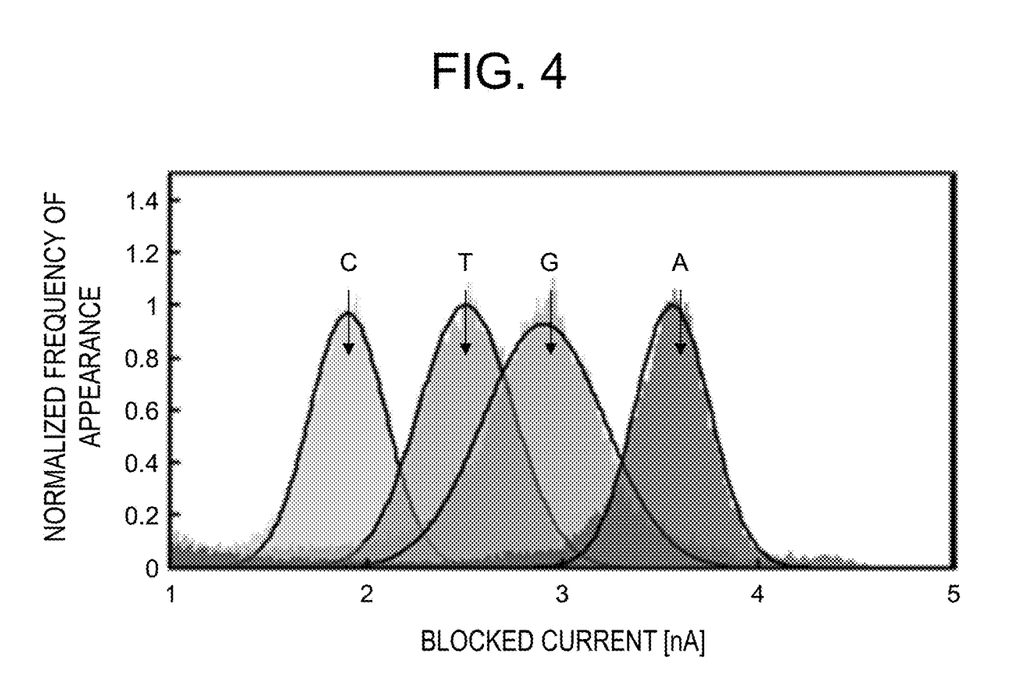
FIG. 4 is a graph showing experimental results of improvements in the degree of base separation according to the present invention.

Hereinafter, embodiments of the present invention will be described with reference to the drawings. According to the present invention, in a nanopore device for analyzing a biopolymer according to a so-called blocked current method, a measurement solution which is brought into contact with a thin film having a nanopore contains cesium as electrolyte cations, and has a pH equal to or greater than pKa of a guanine base (N–1 position). A guanine tetramer (G-quadruplex) forms a planar annular aggregate via a hydrogen bond between the guanine bases as a driving force, and a metal ion then coordinates in a void at the center of the aggregate, so that a robust higher-order structure having a layer of dense aggregates is formed (Example 1 and FIG. 2(a)). Potassium ions having an ion diameter closest to the size of the void are known to form the most robust G-quadruplex. Then, by setting the pH of the measurement solution to be equal to or higher than the pKa of the guanine base (N–1 position), hydrogen present at the N–1 position of the guanine base is deprotonated (FIG. 2(b)). This causes the hydrogen bond between the guanine bases to weaken, which causes an aggregate forming force to weaken. Furthermore, by using cesium ions having an ion diameter greatly different from that of potassium ions as the electrolyte cations, metal ions are less likely to be coordinated at the center of the annular aggregate, and the formation of the G-quadruplex can be inhibited in a state where cations for ensuring electric conductivity coexist (FIG. 2(c)). As a result, the use of the measurement solution having the above component allows blocked current derived from the guanine base to be stably measured over a long period of time without blocking the nanopore even in a guanine base homopolymer (Example 1, FIG. 3), and allows the amount of blocked current derived from each base type to separate, to accurately analyze monomer sequence (FIG. 4).

In one aspect, the present invention relates to a measurement reagent for analyzing a biopolymer containing a nucleic acid by passing the biopolymer through a nanopore formed in a thin film and analyzing the biopolymer based on a change in an electrical signal, the measurement reagent containing a measurement solution which has a pH equal to or greater than pKa of a guanine base and contains cesium ions as electrolyte cations.

As a solvent for the solution, a solvent, which can stably disperse the biopolymer, does not dissolve an electrode, and does not inhibit electron transfer with the electrode, may be used. Examples thereof include water, alcohols (methanol, ethanol, and isopropanol and the like), acetic acid, acetone, acetonitrile, dimethylformamide, and dimethylsulfoxide. When the nucleic acid is used as the biopolymer to be measured, water may be most preferable.

According to the present invention, an electrolyte of the solution contains cesium ions as cations. Cations other than the cesium ions may be added to ensure electric conductivity, but metal ions such as potassium ions promote the three-dimensional conformation of the biopolymer containing a nucleic acid, so that it may be preferable that metal ions other than the cesium ions are not contained as much as possible. Organic cations containing organic substances can be used as substitute cations for metal ions, and ionizing cations typified by ammonium ions and the like can be used, for example. As anions, ionizing anions can be used, and the anions may preferably be selected according to compatibility with an electrode material. For example, when silver halide is used as the electrode material, halide ions (chloride ions, bromide ions, iodide ions) may preferably be used as anions. Alternatively, the anions may be organic anions typified by glutamic acid ions and the like.

According to the present invention, the pH of the measurement solution may be set to be equal to or greater than the pKa of the guanine base and equal to or less than pH 14. Here, since the pKa of the guanine base (N-1 position) also varies depending on the types of solutes coexisting in the solvent, the pKa is preferably adjusted according to the types of the measurement solutions. Typically, the pKa of the guanine base at the N1 position in an aqueous solution is 9.2 (for example, Fedor, et al., Nature Reviews Molecular Cell Biology, 6 (5): 399-412, 2005).

The upper limit of the pH of the measurement solution may be determined by the tolerance limit of the device. When silicon wafers typically used in a semiconductor nanopore are used as substrates and cesium ions coexist, the tolerance limit of the device may be at around pH 14 at which etching of silicon starts. Such an etching rate has already been disclosed (Lloyd D. Clark, et al. Cesium Hydroxide (CsOH): A Useful Etchant for Micromachining Silicon, Technical Digest, Solid-State Sensor and Actuator Workshop, IEEE, 1988). In this case, silicon nitride, which is often utilized as a thin film material, is not etched even at a pH in a high alkali range, but silicon or silicon oxide as a base is etched, so that the upper limit value of the pH may preferably be set to 14. Other semiconductor material is similarly limited by the device tolerance limit of the material.

Examples of a means for adjusting the pH of the measurement solution include a method for adding a hydroxide solution or adding a pH adjuster. Here, the pH adjuster refers to a compound which receives hydrogen ions from a solvent to become cations. In one embodiment, it may be preferable to adjust the pH of the measurement solution by adding cesium hydroxide as the hydroxide solution. This is because the addition of metal ions other than cesium ions promotes the three-dimensional conformation of the biopolymer. That is, the pH of the measurement solution may be adjusted to be equal to or greater than the pKa of the guanine base and equal to or less than pH 14 by adding the cesium hydroxide.

In another embodiment, the pH of the measurement solution may preferably be adjusted by using a compound capable of adjusting the pH of the measurement solution to be equal to or greater than the pKa of the guanine base (N-1 position) as the pH adjuster according to the equation of Henderson-Hasselbalch: $pH=pKa+\log_{10}[HX^+]/[X]$, wherein X refers to the pH adjuster. More specifically, by a compound having pKa equal to or greater than about pH 7.0, the pH of the measurement solution can be set to be equal to or greater than the pKa of the guanine base (N-1 position). For example, since trishydroxymethylaminomethane has pKa of 8.2, and an ionization degree in an aqueous solution having a concentration of 100 mM is about 0.5%, $pH=pKa+\log_{10}[HX^+]/[X]=8.2+2.3=10.5$ is provided from the equation of Henderson-Hasselbalch. Therefore, the pH can be adjusted to be equal to or greater than the pKa of the guanine base (N-1 position). Examples of other compounds include ammonia, chain alkylamines, and cyclic alkylamines. The pH of the measurement solution may be adjusted to be equal to or greater than the pKa of the guanine base (N-1 position) and equal to or less than pH 14 by the pH adjuster according to the equation of Henderson-Hasselbalch $pH=pKa+\log_{10}[HX^+]/[X]$, wherein X refers to the pH adjuster.

When the measurement solution is brought into contact with the atmosphere, a phenomenon occurs in which the measurement solution reacts with carbon dioxide in the atmosphere to cause the pH of the solution to gradually shift to an acidic side. In order to reduce the influence of the carbon dioxide, the pH may be set from the initial state to a higher alkaline side, or the concentration of the pH adjuster may be increased. Specifically, when pH adjusters of 10 mM and 100 mM are used, the pH adjuster of 100 mM increases a time until a pH equal to or less than the pKa of the guanine base is arrived from the same pH, so that the concentration of the pH adjuster is preferably higher, preferably equal to or greater than 50 nM, and more preferably equal to or greater than 100 mM.

In addition, the lower limit of the electrolyte concentration may preferably be provided from the viewpoint of a signal-to-noise ratio (Example 1, FIG. 4). Therefore, according to the present invention, the lower limit of the electrolyte concentration needs to be 10 mM. On the other hand, there is no requirement to suppress the upper limit of the electrolyte concentration, which allows the saturation concentration to be accepted. That is, the cesium ion concentration of the measurement solution may be equal to or greater than 10 mM and equal to or less than the saturated concentration.

The measurement solution used in the present invention can be prepared according to a known method. For example, the measurement solution can be prepared by dissolving an electrolyte in a solvent to obtain a solution, and thereafter adjusting the pH of the solution using an appropriate means.

The measurement reagent for analyzing the biopolymer according to the present invention contains the above-described measurement solution as a component. The measurement reagent may be provided together with the instructions describing a procedure and an amount for use and the like. The measurement solution may be provided in a ready-to-use state (liquid), as a concentrated solution for dilution with an appropriate solvent upon use, or in a solid state (for example, powder and the like) for reconstitution with a suitable solvent upon use. The form and preparation of such measurement reagent can be recognized by those skilled in the art.

The present invention also relates, in another aspect, to a device for analyzing a biopolymer. In one embodiment, the present invention provides a device for analyzing a biopolymer containing a nucleic acid, the device including: a thin film having a nanopore; a pair of containers capable of storing a measurement solution which is brought into contact with the thin film; and a pair of electrodes provided in each of the containers, wherein: the measurement solution is introduced into each of the containers so as to be brought into contact with the thin film; and the measurement solution has a pH equal to or greater than pKa of a guanine base and contains cesium ions as electrolyte cations.

In another embodiment, the present invention provides a device for analyzing a biopolymer containing a nucleic acid, the device including: an array device including a plurality of thin film parts having a nanopore; a single common container and a plurality of individual containers capable of storing a measurement solution which is brought into contact with the thin films; and individual electrodes respectively provided in the plurality of individual containers, wherein: the measurement solution is introduced into each of the individual containers and the common container so as to be brought into contact with the thin films; and the measurement solution has a pH equal to or greater than pKa of a guanine base and contains cesium ions as electrolyte cations.

A nanopore device for analyzing a biopolymer according to a so-called blocked current method has been known in the art, and its constituents can also be readily understood by those skilled in the art. For example, specific devices are disclosed in Non-Patent Literatures 1 and 2, U.S. Pat. No. 5,795,782 B; Yanagi, et al., Scientific Reports 4, 5000, 2014; Akahori, et al., Nanotechnology 25 (27): 275501, 2014; Yanagi, et al., Scientific Reports, 5, 14656, 2015; and Goto, et al., Scientific Reports 5, 16640, 2015.

A thin film having a nanopore may be a lipid bilayer (biopore) consisting of amphipathic molecular layers in which a protein having a pore at its center is embedded, or a thin film (solid pore) consisting of a material which can be formed by a semiconductor microfabrication technique. Examples of the material which can be formed by the semiconductor microfabrication technique include silicon nitride (SiN), silicon oxide ($SiO_2$), silicon oxynitride (SiON), hafnium oxide ($HfO_2$), molybdenum disulfide ($MoS_2$), and graphene. The thickness of the thin film may be 1 Å to 200 nm, preferably 1 Å to 100 nm, more preferably 1 Å to 50 nm, for example, about 5 nm.

The appropriate size of the nanopore (pore) can be selected according to the types of biopolymers to be analyzed, and is, for example, 0.9 nm to 100 nm, preferably 0.9 nm to 50 nm, and specifically equal to or greater than about 0.9 nm and equal to or less than 10 nm. The diameter of ssDNA (single-stranded DNA) is about 1.5 nm, and the appropriate range of the pore diameter for analyzing ssDNA may be about 1.5 nm to 10 nm, preferably about 1.5 nm to 2.5 nm, for example about 2 nm. The diameter of dsDNA (double-stranded DNA) is about 2.6 nm, and the appropriate range of the pore diameter for analyzing dsDNA may be about 3 nm to 10 nm, and preferably about 3 nm to 5 nm. The depth of the nanopore can be adjusted by adjusting the thickness of the thin film. The depth of the nanopore may be twice or more, preferably three times or more, and more preferably five times or more of the size of a monomer unit constituting the biopolymer. For example, when the biopolymer contains the nucleic acid, the depth of the nanopore may preferably be the size of three or more bases, for example, equal to or greater than about 1 nm. This allows the biopolymer to enter the nanopore while controlling its shape and moving speed, thereby enabling analysis with high sensitivity and high accuracy. The shape of the pore is basically a circle, but the pore can also have an oval shape or a polygonal shape. When the array device including a plurality of thin film parts having a nanopore is used, it may be preferable that the thin film parts having a nanopore are regularly arranged. Intervals at which the plurality of thin film parts are disposed can be set to 0.1 µm to 10 µm, and preferably 0.5 µm to 4 µm, depending on the electrode to be used and the capability of an electric measurement system.

The method for forming a nanopore (pore) in the thin film is not particularly limited, and electron beam irradiation from a transmission electron microscope and the like, and insulation breakdown from voltage application, and the like can be used, for example.

The container (including the individual container and the common container) capable of storing the measurement solution which is brought into contact with the thin film can be appropriately provided so as to have a material, a shape and a size which do not affect the measurement of blocked current. The measurement solution is introduced into the container so as to be brought into contact with the thin film.

It may be preferable that the electrode is made of a material capable of performing an electron transfer reaction (Faraday reaction) with the electrolyte in the measurement solution, and typically the electrode is made of silver halide or alkali silver halide. From the viewpoints of potential stability and reliability, silver/silver chloride may preferably be used as the electrode. The electrode may be made of a material serving as a polarizing electrode, and may be made of, for example, gold or platinum and the like. In that case, it is preferable to add a substance capable of assisting an electron transfer reaction such as potassium ferricyanide or potassium ferrocyanide to the measurement solution in order to secure stable ionic current. Alternatively, substances capable of performing an electron transfer reaction, such as ferrocenes, are preferably fixed on the surface of a polarizing electrode. In the structure of the electrode, the electrode may be wholly made of the material mentioned above, or the material may be coated on the surface of a base material (such as copper or aluminum). The shape of the electrode is not particularly limited, but the shape of the electrode may be preferable such that the surface area of the electrode which is brought into contact with the measurement solution is larger. The electrode is joined to wires, which causes electrical signals to be sent to a measurement circuit.

The analysis device according to the present invention may further include an inlet for introducing the measurement solution into each of the containers.

In a preferred embodiment, the common container may have a common electrode, and the individual electrodes may be connected to a data processing substrate via a wire. In another preferred embodiment, the common container has an opening, and the analysis device according to the present invention further includes a holding substrate having a surface on which the biopolymer is fixed and a mechanism for driving the holding substrate.

Furthermore, the present invention relates to also a method for analyzing a biopolymer containing a nucleic acid. The biopolymer to be analyzed using the measurement reagent or the analysis device according to the present invention or in the method according to the present invention may be any object which changes electrical characteristics, in particular, a resistance value, when passing through the nanopore, and includes a nucleic acid. Specific examples thereof include RNA (single-stranded RNA or double-stranded RNA), DNA (single-stranded DNA or double-stranded DNA), PNA (peptide nucleic acid), oligonucleotide, aptamer, and a combination thereof (hybrid nucleic acid). The biopolymer may be present in a living body, or may be derived from one present in the living body. Examples thereof include polymers containing sequences and constituents not naturally occurring, such as sequences of poly (A) and poly (T) and the like, artificially synthesized polymer molecules, nucleic acids prepared by a nucleic acid amplification technique (for example, PCR), and nucleic acids cloned into vectors. The methods for preparing the biopolymers are well known in the art, and those skilled in the art can appropriately select a preparation method according to the types of the biopolymers.

According to the present invention, "analysis" of the biopolymer refers to characteristic analysis of the nucleic acid constituting the biopolymer. For example, the "analysis" refers to analysis of the sequence order (sequencing) of the monomers of the nucleic acid constituting the biopolymer, determination of the length of the nucleic acid, detection of single base polymorphism, determination of the number of biopolymers, and detection of structure polymorphism in the biopolymer (copy number polymorphism, insertion, and deletion and the like).

In one embodiment, the method according to the present invention includes the steps of: passing a biopolymer containing a nucleic acid through a nanopore formed in a thin film in a measurement solution having a pH equal to or greater than pKa of a guanine base and containing cesium ions as electrolyte cations; and analyzing the biopolymer based on a change in an electrical signal.

In another embodiment, the method according to the invention may be carried out by using the analysis device described above, and includes the steps of: passing the biopolymer containing a nucleic acid through a nanopore under a condition in which the measurement solution described above is brought into contact with the thin film of the analysis device; measuring an electrical signal by an electrode; and analyzing the biopolymer based on a change in an electrical signal.

The analysis method according to the present invention can be carried out by using the same apparatuses, processes and conditions as those of a conventional method except that the measurement solution having a pH equal to or greater than pKa of a guanine base and containing cesium ions as electrolyte cations is used. By using such measurement solution, the three-dimensional conformation (particularly, the tetramer of the guanine base, G-quadruples) of the biopolymer containing a nucleic acid can be eliminated, which allows the blocked current in the nanopore to be accurately and correctly measured. An ionic current difference between monomers increases, which improves the degree of base separation, thereby allowing the biopolymer to be analyzed with high accuracy.

EXAMPLES

Hereinafter, the present invention will be described in more detail by way of Examples, but the present invention is not limited to these Examples.

Example 1

Figure 1:
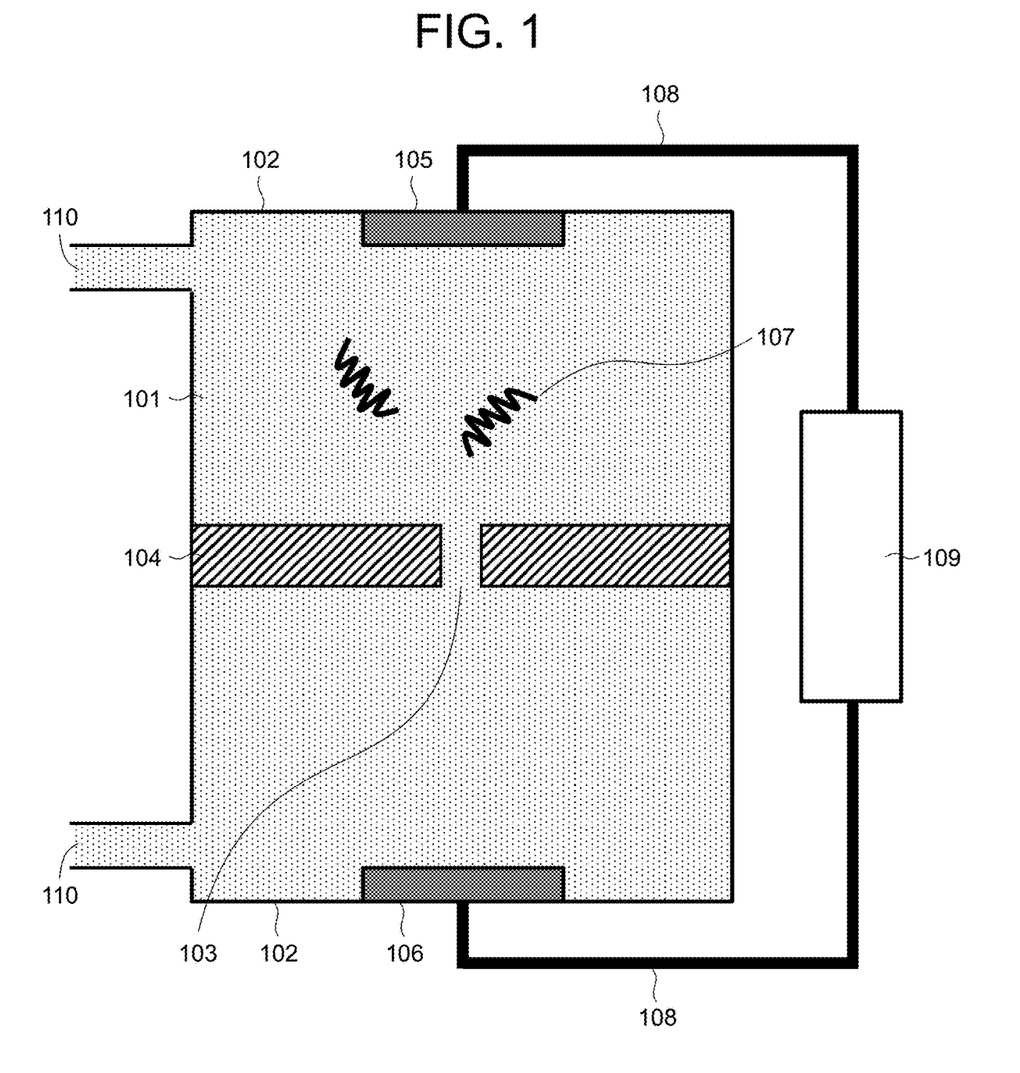
FIG. 1 is a diagram showing an embodiment of the constitution of an analysis device according to the present invention.

FIG. 1 shows an example of a constitution diagram of an analysis device using a single nanopore according to the present invention.

The device includes two containers 102 capable of storing a solution 101, a thin film 104 having a nanopore 103, and two electrodes 105 and 106. Each of the two electrodes is installed in each of the containers so that the electrodes face each other with the nanopore sandwiched therebetween. The solution contained in each of the two containers contains an electrolyte, and it is only necessary that the solution contained in at least one of the containers contains a biopolymer 107 containing a nucleic acid to be measured. Ion current passing through the nanopore is measured by a measurement system 109 via a wire 108 joined to the two electrodes. The solution is filled through an inlet 110. Typically, the measurement system includes an ionic current measurement device, an analog digital output conversion device, a data processing device, a data display output device, and an input/output auxiliary device. The ionic current measurement device is equipped with a current-voltage converting type high-speed amplifying circuit, and the data processing device is equipped with a computing device, a temporary memory device, and a nonvolatile memory device. In order to reduce external noise, the analysis device may preferably be covered with a Faraday cage.

A biopolymer containing a nucleic acid may be any object which changes electrical characteristics, in particular, a resistance value, when passing through the nanopore. Typical examples thereof include single-stranded DNA, double-stranded DNA, RNA, PNA (peptide nucleic acid), oligonucleotide, and a combination thereof (for example, hybrid nucleic acid). When a monomer sequence is to be analyzed in the device, the biopolymer needs to take the form of a linear polymer having an eliminated higher order structure. A means for passing an object to be measured through the nanopore may preferably be transportation according to electrophoresis, but it may be a solvent flow generated by a pressure potential difference and the like.

The nanopore 103 may be a hole having the minimum size which allows the object to be measured to pass through. When a single-stranded DNA is an object to be measured as the biopolymer, the nanopore may be a hole having a diameter of about 0.9 nm to 10 nm which allows the single-stranded DNA to pass through, and the thickness of the thin film may be several angstroms to several tens of nanometers. The nanopore may be a biopore or a solid pore. In the case of the biopore, preferred is a protein having a center pore embedded in an amphipathic molecular layer capable of forming a lipid bilayer as a thin film. In the case of the solid pore, the material of the thin film may be any material which can be formed by a semiconductor microfabrication technique. Typically, the material may be silicon nitride, silicon oxide, hafnium oxide, molybdenum disulfide, and graphene and the like. In this case, examples of the method for forming a pore in the thin film include electron beam irradiation from a transmission electron microscope and the like, and insulation breakdown from voltage application.

The electrode may preferably be made of a material capable of performing an electron transfer reaction (Faraday reaction) with an electrolyte in a measurement solution, and typically, the electrode may be made of silver halide or alkali silver halide. Among them, silver/silver chloride is desirable from the viewpoints of potential stability and reliability. However, other material may be a material serving as a polarizing electrode, and may be, for example, gold or platinum and the like. In that case, it is preferable to add a substance capable of assisting an electron transfer reaction such as potassium ferricyanide or potassium ferrocyanide to the measurement solution in order to secure stable ionic current. Alternatively, substances capable of performing an electron transfer reaction, such as ferrocenes, are preferably fixed on the surface of the polarizing electrode.

In the structure of the electrode, the electrode may be wholly made of the material mentioned above, or the material may be coated on the surface of a base material (such as copper or aluminum).

The electrode may be joined to a wire, which causes electrical signals to be sent to a measurement circuit. The shape of the electrode may be any shape, but the shape of the electrode may be preferable such that the surface area of the electrode which is brought into contact with the solution is larger.

The solvent for the solution may be any solvent which can stably disperse the biopolymer, does not dissolve the electrode, and does not inhibit electron transfer with the electrode. Examples thereof include water, alcohols (methanol, ethanol, and isopropanol and the like), acetic acid, acetone, acetonitrile, dimethylformamide, and dimethylsulfoxide. When the nucleic acid is used as the biopolymer to be measured, water may be most preferable.

It is only necessary that the solvent contains cesium ions as electrolyte cations. Cations other than the cesium ions may be added to ensure electric conductivity, but metal ions such as potassium ions promote the three-dimensional conformation of the biopolymer containing a nucleic acid, so that it may be preferable that metal ions other than the cesium ions are not contained as much as possible. Substitute cations for metal ions are preferably organic cations containing organic substances. For example, the cations may be ionizing cations typified by ammonium ions and the like. Anions may be ionizing anions, and the anions may preferably be selected according to compatibility with an electrode material. For example, when silver halide is used as the electrode material, halide ions (chloride ions, bromide ions, iodide ions) may preferably be used as anions. Alternatively, the anions may be organic anions typified by glutamic acid ions and the like.

The pH of the solution needs to be equal to or greater than the pKa of a guanine base (N-1 position). As shown in FIG. 2(a), a guanine tetramer (G-quadruplex) forms a planar annular aggregate via a hydrogen bond between the guanine bases as a driving force, and a metal ion then coordinates in a void at the center of the aggregate, so that a robust higher-order structure having a layer of dense aggregates is formed. Potassium ions having an ion diameter closest to the size of the void are known to form the most robust G-quadruplex. Then, by setting the pH of the measurement solution to be equal to or greater than the pKa of the guanine base (N-1 position), hydrogen present at the N-1 position of the guanine base is deprotonated, as shown in FIG. 2(b). This causes the hydrogen bond between the guanine bases to weaken, which causes an aggregate forming force to weaken. Furthermore, by using cesium ions having an ion diameter greatly different from that of potassium ions, a metal ion is less likely to be coordinated at the center of the annular aggregate, and the formation of the G-quadruplex can be inhibited in a state where cations for ensuring electric conductivity coexist, as shown in FIG. 2(c). Since the pKa of the guanine base (N-1 position) also varies depending on the types of solutes coexisting in the solvent, the pKa may preferably be adjusted according to the types of the measurement solutions. Typically, the literature (Fedor, et al., Nature Reviews Molecular Cell Biology, 6 (5): 399-412, 2005) discloses that the pKa of a guanine base at an N1 position in an aqueous solution is 9.2.

The upper limit of the pH of the solution may be determined by the tolerance limit of the device. In a semiconductor nanopore, silicon wafers are typically used as substrates. When cesium ions coexist, the tolerance limit of the device may be at around pH 14 at which etching of silicon starts. Such an etching rate is disclosed in the literature (Lloyd D. Clark, et al. Cesium Hydroxide (CsOH): A Useful Etchant for Micromachining Silicon, Technical Digest, Solid-State Sensor and Actuator Workshop, IEEE, 1988). In this case, silicon nitride, which is often utilized as a thin film material, is not etched even at a pH in a high alkali range, but silicon or silicon oxide as a base is etched, so that the upper limit value of the pH may preferably be set to 14. Other semiconductor material is similarly limited by the device tolerance limit of the material.

Examples of a means for adjusting the pH of the solution include a method for adding a hydroxide solution or adding a pH adjuster. Here, the pH adjuster refers to a compound which receives hydrogen ions from a solvent to become cations.

Since the addition of metal ions other than cesium ions promotes the three-dimensional conformation of the biopolymer, it is necessary to adjust the pH of the solution by adding cesium hydroxide as the hydroxide solution.

The pH adjuster may be a compound capable of adjusting the pH of the measurement solution to be equal to or greater than the pKa of the guanine base (N-1 position) according to the equation of Henderson-Hasselbalch: $pH=pKa+\log_{10}[HX^+]/[X]$, wherein X refers to the pH adjuster. More specifically, by a compound having pKa equal to or greater than about pH 7.0, the pH of the measurement solution can be set to be equal to or greater than the pKa of the guanine base (N-1 position). For example, since trishydroxymethylaminomethane has pKa of 8.2, and an ionization degree in an aqueous solution having a concentration of 100 mM is about 0.5%, $pH=pKa+\log_{10}[HX^+]/[X]=8.2+2.3=10.5$ is provided from the equation of Henderson-Hasselbalch. Therefore, the pH can be adjusted to be equal to or greater than the pKa of the guanine base (N-1 position). Examples of other compounds include ammonia, chain alkylamines, and cyclic alkylamines.

When the solution is brought into contact with the atmosphere, a phenomenon occurs in which the solution reacts with carbon dioxide in the atmosphere to cause the pH of the solution to gradually shift to an acidic side. In order to reduce the influence of the carbon dioxide, the pH may be set from the initial state to a higher alkaline side, or the concentration of the pH adjuster may be increased. Specifically, when pH adjusters of 10 mM and 100 mM are used, the pH adjuster of 100 mM increases a time until a pH equal to or less than the pKa of the guanine base is arrived from the same pH, so that the concentration of the pH adjuster is preferably higher.

In addition, the lower limit of the electrolyte concentration may preferably be provided from the viewpoint of a signal-to-noise ratio. As will be described later, it is revealed according to the present invention that, in a solution containing 1 M cesium ions, a difference in blocked current amount between bases is about 500 pA as shown in FIG. 4. The difference in blocked current amount positively depends on the electric conductivity of the nanopore. It is known that, when water is used as a solvent, the electric conductivity approximately linearly responds to an electrolyte concentration of up to about 1 mM as disclosed in the literature (Ralph M. M. Smeets, et al., Salt Dependence of Ion Transport and DNA Translocation through Solid-State Nanopores, Nano Lett 6, 89, 2006). Therefore, when the electrolyte concentration is decreased by one order of magnitude, the difference in blocked current amount is also decreased by one order of magnitude. Therefore, the difference in blocked current amount between bases decreases to 50 pA in 100 mM cesium ions, 5 pA in 10 mM, and 0.5 pA in 1 mM. Meanwhile, current noise occurring during measurement can be roughly divided into two types of noise derived from the device and noise derived from an amplifier. However, even if the noise derived from the device is reduced by measures such as reduction in capacitance, it is difficult to reduce the current noise to be equal to or smaller than the noise derived from the amplifier. Therefore, the lower limit of the electrolyte concentration is defined by the noise derived from the amplifier, but as disclosed in the literature (Adrian Balan, et al. Improving Signal-to-Noise Performance for DNA Translocation in Solid-State Nanopores at MHz Bandwidths, Nano Lett. 14, 7215, 2014), in a frequency range (5 to 10 kHz) to be frequently used, the noise derived from the amplifier is about 1 pA. Therefore, since five is often defined as a statistically significant signal-to-noise ratio, the lower limit of the electrolyte concentration according to the present invention needs to be 10 mM. On the other hand, there is no requirement to suppress the upper limit of the electrolyte concentration, which allows the saturation concentration to be accepted.

The constitution of the present invention makes it possible to eliminate the three-dimensional conformation of the biopolymer containing a nucleic acid and to improve the difference in blocked current amount between the monomers. FIG. 3 shows experimental results comparing a conventional method with a method using a measurement reagent or an analysis device according to the present invention. A device having a 5-nm-thick thin film having a nanopore of 2 nm (for example, a structure disclosed in Yanagi, I. et al. Fabrication of 3-nm-thick $Si_3N_4$ membranes for solid-state nanopores using the poly-Si sacrificial layer process, Scientific Reports, 5, 14656, 2015), and a pair of silver/silver chloride electrodes and a high-speed current measuring amplifier are combined. As a measurement solution, a conventional 1 M aqueous potassium chloride solution having a pH of 7 and a 1 M aqueous cesium chloride solution adjusted to a pH of 11 by 100 mM trishydroxymethylaminomethane according to the present invention were compared with each other. Measurement samples using 30-mer poly (dA), poly (dC), poly (dT), and poly (dG) were used for verification. First, as a result of starting measurement of the 30-mer poly (dG) in the conventional measurement solution at an applied voltage of 300 mV, as shown in FIG. 3(a), it was revealed that the ion current immediately drops to zero. This means that the nanopore is blocked by the guanine (G) tetramer, which means that the blocked current amount of the guanine base cannot be accurately measured. Meanwhile, as a result of starting measurement of the 30-mer poly (dG) in the measurement solution of the present invention at an applied voltage of 300 mV, as shown in FIG. 3(b), it was confirmed that the nanopore is not blocked, and the blocked current derived from the guanine base can be stably measured over a long period of time. In addition, the blocked current amount was similarly measured for other base types, the 30-mer poly (dA), poly (dC) and poly (dT). As a result, as shown in FIG. 4, it was confirmed that the blocked current amount derived from each base type is separated, which allows the analysis accuracy of the monomer sequence to be improved.

Furthermore, in order to compare the effect of cesium ions according to the present invention with that of other cationic species, the present inventors particularly paid attention to cations of alkali metals, and verified whether the three-dimensional conformation of the 30-mer poly (dG) can be eliminated. Specifically, by using a 1 M aqueous lithium chloride solution, a 1 M aqueous potassium chloride solution, and a 1 M aqueous rubidium chloride solution adjusted to a pH of 11 by 100 mM trishydroxymethylaminomethane, 30-mer poly (dG) passage through a nanopore was measured in a device having a 5-nm-thick thin film having a nanopore of 2 nm. As a result, it was confirmed that, in all the solutions except the 1 M aqueous cesium chloride solution having a pH of 11, the ion current immediately becomes zero as with FIG. 3(a), and the nanopore is blocked by the G-quadruplex. Therefore, it was shown that the three-dimensional conformation cannot be eliminated only by changing the pH to be equal to or greater than the pKa of the guanine base (N–1 position), and the presence of the cesium ions is important for exhibiting the effect.

Example 2

Figure 5:
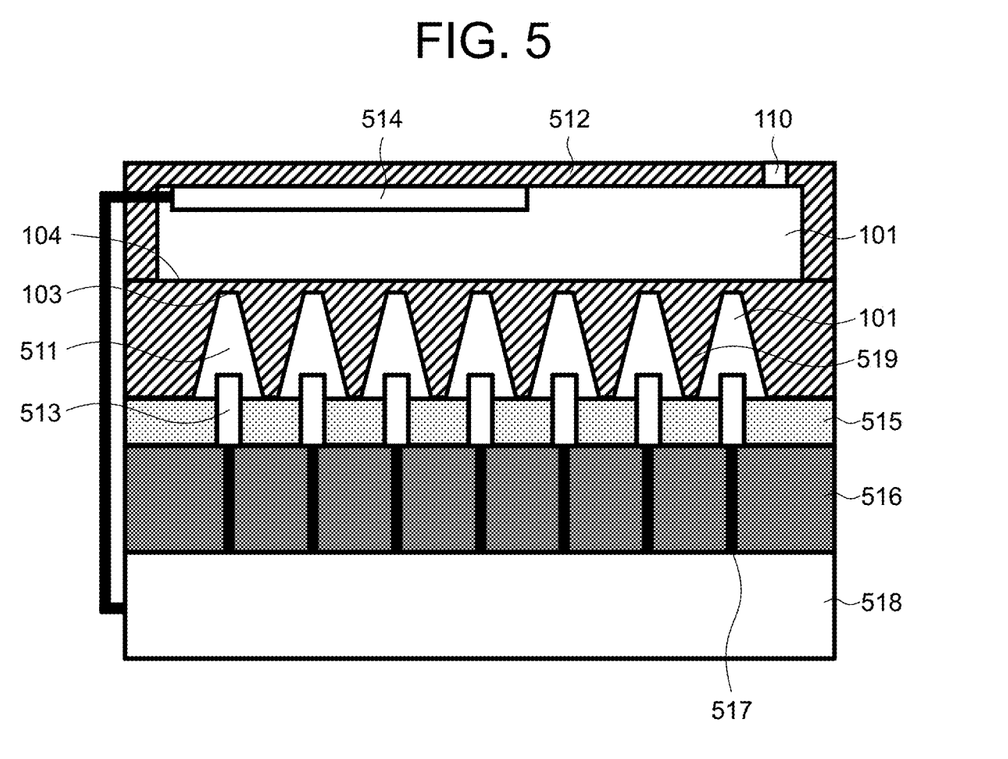
FIG. 5 is a diagram showing another embodiment of the constitution of the analysis device according to the present invention.

FIG. 5 shows an example of a constitution diagram of another embodiment of the analysis device according to the present invention. In FIG. 1, an example in the case of having a single nanopore was shown, but in FIG. 5, an example in the case of parallelizing nanopores was shown. A plurality of individual containers 511 capable of storing a solution are prepared, and an array device in which a plurality of thin films 104 each having a nanopore 103 are parallelized is provided. A single common container 512 is provided, via the thin films, on the opposite side of the plurality of individual containers. An individual electrode 513 is provided in each of the plurality of individual containers. It is preferable that the nanopores and the plurality of individual layers correspond one on one, and are parallelized by the number. A common electrode 514 is disposed in the common container at a position facing the nanopore. Each individual electrode is embedded and set in an electrode substrate 515. The individual electrode is connected to a data processing substrate 518 via an independent wire 517 provided on a wire substrate 516, and ion current is independently observed for each individual electrode. In order to improve the measurement accuracy, the nanopores are insulated from each other by a septum 519 in order to suppress current crosstalk between the nanopores. The solution containing the object to be measured is typically introduced in a container located on a common electrode side via an inlet 110.

The same contents as those mentioned in Example 1 may be used for the solution. As with the case described in Example 1, effects of eliminating the three-dimensional conformation of the biopolymer containing a nucleic acid and improving the degree of base separation are exhibited according to the present example. The present example allows measurements to be performed in parallel, so that the monomer sequence of the biopolymer can be analyzed with very high throughput while high analysis accuracy is maintained.

Example 3

Figure 6:
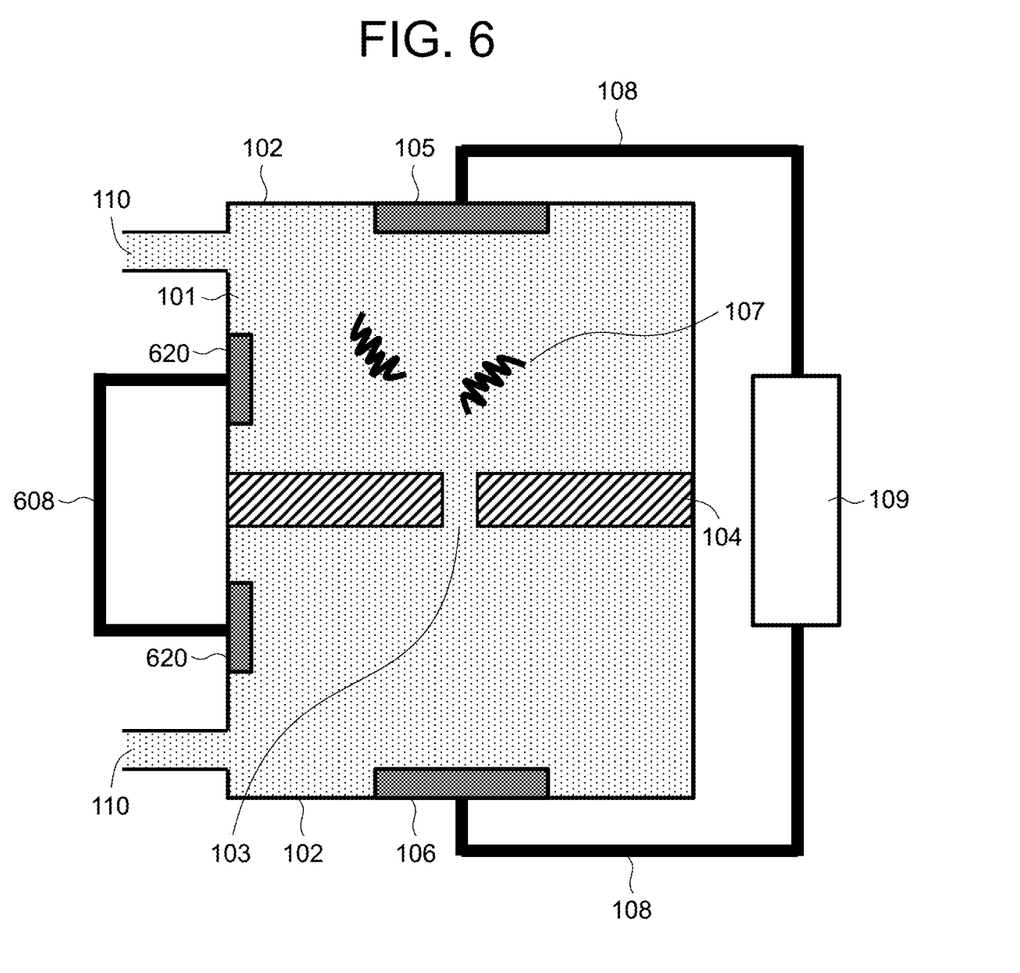
FIG. 6 is a diagram showing another embodiment of the constitution of the analysis device according to the present invention.

FIG. 6 shows an example of a constitution diagram of another embodiment of the analysis device according to the present invention.

A thin film for biopolymer measurement is susceptible to a potential difference between solutions located on both sides of the thin film, which may cause the thin film to be broken by the potential difference. In particular, when the electrostatic capacitance of the analysis device is lowered in order to reduce noise current, the thin film is apt to be broken. When a solution is placed in each of solution containers located on both sides of the thin film, an initial charge difference ΔQ necessarily occurs between the solutions, so that the potential difference ΔV (=ΔQ/C) applied to the thin film by reduction in the electrostatic capacitance C of the analysis device is amplified, which causes the insulation breakdown of the thin film to occur, thereby causing the thin film breakdown phenomenon. Then, in order to avoid the breakdown phenomenon, a pair of electrodes are newly disposed in addition to ion current measurement electrodes on both sides of the thin film, whereby the charge difference can be reduced to prevent the thin film breakdown. FIG. 6 shows a constitution diagram in which two electrodes 620 for reducing the charge difference are added to the constitution of FIG. 1. The two electrodes 620 are electrically connected via a wire 608. The constitution is described in detail in Matsui, K., et al., Scientific Reports 5, 17819, 2015, for example.

The same contents as those mentioned in Example 1 may be used for the solution. As with the case described in Example 1, effects of eliminating the three-dimensional conformation of a biopolymer containing a nucleic acid and improving the degree of base separation are also exhibited according to the present example.

Example 4

Figure 7:
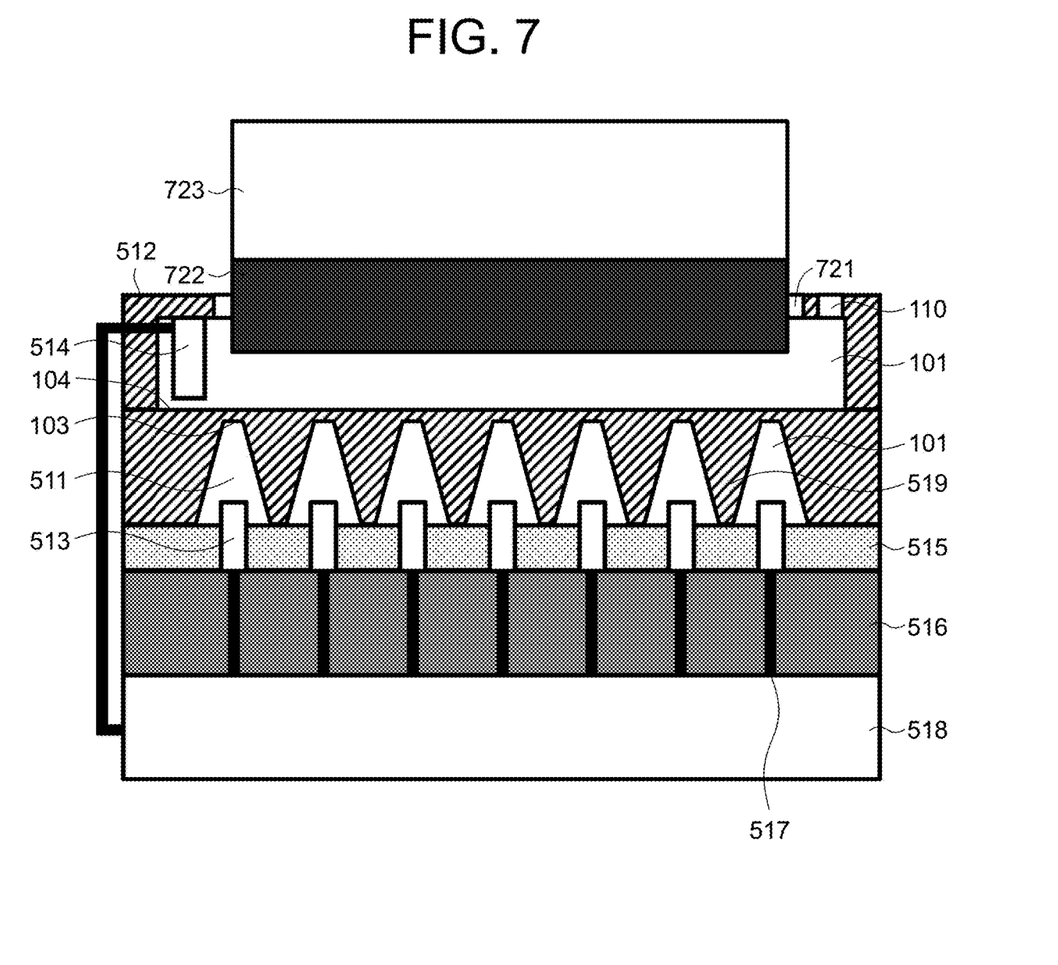
FIG. 7 is a diagram showing another embodiment of the constitution of the analysis device according to the present invention.

FIG. 7 shows an example of a constitution diagram of another embodiment of the analysis device according to the present invention.

FIG. 7 shows a constitution in which an opening 721 of a common container, a substrate 722, and a driving mechanism 723 for driving a substrate position are added to the constitution of FIG. 5. A biopolymer is fixed on the substrate 722, and the relative position of an object to be measured with respect to a nanopore 103 can be optionally and precisely controlled by the driving mechanism 723 via an external control system. The driving mechanism may preferably be a piezoelectric element and a motor. Alternatively, the object to be measured may be fixed to a cantilever, and driven as in an atomic force microscope. Such constitution is described, for example, in the literature (E. M. Nelson, et al., ACS Nano, 8(6), 5484, 2014). When the object to be measured is a biopolymer containing a nucleic acid, it is preferable to precisely move the biopolymer for each monomer in order to analyze monomer sequence. The same contents as those mentioned in Example 1 may be used for the solution. As with the case described in Example 1, effects of eliminating the three-dimensional conformation of a biopolymer containing a nucleic acid and improving the degree of base separation are also exhibited according to the present example. The constitution of the present example makes it possible to precisely control the object to be measured, thereby improving the measurement accuracy.

Example 5

An example of a procedure for analyzing a biopolymer using a measurement reagent or an analysis device according to the present invention will be described below. Here, the analysis method of the present invention is a method for analyzing a biopolymer containing a nucleic acid, and includes the steps of: passing a biopolymer containing a nucleic acid through a nanopore formed in a thin film in a measurement solution having a pH equal to or greater than pKa of a guanine base and containing cesium ions as electrolyte cations; and analyzing the biopolymer based on a change in an electrical signal.

By using the analysis method, nucleic acid monomers in the biopolymer containing a nucleic acid can be sequenced. When the biopolymer passes through the nanopore, the electrical signal changes according to the types of the bases, so that the sequence can be determined according to the pattern of the electrical signal. Such method is disclosed in detail in the literature (A. H. Laszlo, et al., Nat. Biotechnol. 32, 829, 2015), for example.

By using the analysis method, the length of the biopolymer can be determined based on the total signal change number of the electrical signal pattern. As another application, the number of the biopolymers contained in the solution can also be determined by the total number of the biopolymers passing through the nanopore.

The present invention is not limited to the above-described Examples, and various modifications are encompassed in it. For example, the above-described Examples have been described in detail for a better understanding of the present invention, and are not necessarily limited to those having all the constitutions of the description. Additionally, it is possible to replace a part of the configuration of certain Example with the configuration of another Example, and it is also possible to add the configuration of certain Example to the configuration of another Example. Further, regarding a part of the configuration of each Example, addition of another configuration, its deletion, and replacement with another configuration can be performed.

All the publications, patents and patent applications cited herein are incorporated herein by reference as it is.

REFERENCE SIGNS LIST 101 solution
102 container
103 nanopore
104 thin film
105, 106 electrode
107 biopolymer
108 wire
109 measurement system
110 inlet
511 individual container
512 common container
513 individual electrode
514 common electrode
515 electrode substrate
516 wire substrate
517 independent wire
518 data processing substrate
519 septum
608 wire
620 electrode
721 opening
722 substrate
723 driving mechanism

The invention claimed is:

1. A method for analyzing a biopolymer, comprising:
preparing a device comprising: a thin film of a solid state silicon based substrate having a nanopore; a pair of containers capable of storing a measurement solution which is brought into contact with the thin film; and a pair of electrodes provided in each of the containers;
depronating hydrogen present at the N−1 position of the guanine bases, causing the hydrogen bond between the guanine bases to weaken and correspondingly weaken an aggregate forming force among the guanine bases, and using cesium ions as electrolyte cations in the measurement solution for inhibiting the guanine bases from forming a tetramer (G-quadruplex) that blocks the nanopore;

passing a biopolymer comprising a nucleic acid through the nanopore formed in the thin film; and analyzing the biopolymer based on a change in an electrical signal due to the pass of the biopolymer through the nanopore.

2. The method for analyzing a biopolymer according to claim 1, wherein the solution comprises halide ions as electrolyte anions.

3. The method for analyzing a biopolymer according to claim 1, wherein the solution has a pH equal to or greater than pKa of the guanine base and equal to or less than pH 14.

4. The method for analyzing a biopolymer according to claim 1, wherein the solution has a pH adjusted to be equal to or greater than pKa of the guanine base and equal to or less than pH 14 by adding cesium hydroxide.

5. The method for analyzing a biopolymer according to claim 1, wherein the solution has a pH adjusted to be equal to or greater than pKa of the guanine base (N−1 position) and equal to or less than pH 14 by a pH adjuster according to the equation of Henderson-Hasselbalch $pH=pKa+\log 10[HX+]/[X]$, wherein X refers to the pH adjuster.

6. The method for analyzing a biopolymer according to claim 5, wherein the pH adjuster has a concentration equal to or greater than 100 mM.

7. The method for analyzing a biopolymer according to claim 1, wherein the solution has a cesium ion concentration equal to or greater than 10 mM and equal to or less than a saturated concentration.

8. The method for analyzing a biopolymer according to claim 1, wherein the biopolymer is RNA, DNA or PNA, or a combination thereof.

9. The method for analyzing a biopolymer according to claim 1, wherein the substrate is one of silicon nitride (SiN), silicon oxide (SiO2) and silicon oxynitride (SiON).

* * * * *